(12) United States Patent
Holsten et al.

(10) Patent No.: US 7,666,180 B2
(45) Date of Patent: Feb. 23, 2010

(54) GASTRIC RESTRICTOR ASSEMBLY AND METHOD OF USE

(75) Inventors: Henry Holsten, Southington, CT (US); Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 496 days.

(21) Appl. No.: 11/133,618

(22) Filed: May 20, 2005

(65) Prior Publication Data

US 2006/0264983 A1    Nov. 23, 2006

(51) Int. Cl.
*A61B 17/00*  (2006.01)
(52) U.S. Cl. .......................... 606/1; 600/30; 623/23.65
(58) Field of Classification Search .................. 606/1; 623/2.11, 23.65; 600/30
See application file for complete search history.

(56) References Cited

U.S. PATENT DOCUMENTS

| | | | |
|---|---|---|---|
| 3,787,022 A * | 1/1974 | Wilcox | ................. 251/212 |
| 6,358,228 B1 | 3/2002 | Tubman et al. | |
| 6,400,980 B1 | 6/2002 | Lemelson | |
| 6,419,699 B1 | 7/2002 | Schuessler | |
| 6,427,089 B1 | 7/2002 | Knowlton | |
| 6,432,039 B1 | 8/2002 | Wardle | |
| 6,432,040 B1 | 8/2002 | Meah | |
| 6,449,512 B1 | 9/2002 | Boveja | |
| 6,450,173 B1 | 9/2002 | Forsell | |
| 6,450,946 B1 | 9/2002 | Forsell | |
| 6,453,907 B1 | 9/2002 | Forsell | |
| 6,454,698 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,454,785 B2 | 9/2002 | De Hoyos Garza | |
| 6,460,543 B1 | 10/2002 | Forsell | |
| 6,461,292 B1 | 10/2002 | Forsell | |
| 6,461,293 B1 | 10/2002 | Forsell | |
| 6,463,935 B1 | 10/2002 | Forsell | |
| 6,464,698 B1 | 10/2002 | Falwell | |
| 6,471,635 B1 | 10/2002 | Forsell | |
| 6,494,879 B2 | 12/2002 | Lennox et al. | |
| 6,500,110 B1 | 12/2002 | Davey et al. | |
| 6,511,490 B2 | 1/2003 | Robert | |
| 6,511,506 B2 | 1/2003 | Chevillon et al. | |
| 6,540,789 B1 | 4/2003 | Silverman et al. | |
| 6,543,456 B1 | 4/2003 | Freeman | |
| 6,547,801 B1 | 4/2003 | Dargent et al. | |
| 6,558,400 B2 | 5/2003 | Deem et al. | |
| 6,572,627 B2 | 6/2003 | Gabbay | |
| 6,579,225 B2 | 6/2003 | Pregenzer et al. | |
| 6,587,719 B1 | 7/2003 | Barrett et al. | |
| 6,596,004 B1 | 7/2003 | Regnault | |
| 6,609,025 B2 | 8/2003 | Barrett et al. | |
| 6,627,206 B2 | 9/2003 | Lloyd | |
| 6,652,448 B2 | 11/2003 | Migachyov | |
| 6,656,194 B1 | 12/2003 | Gannoe et al. | |

(Continued)

*Primary Examiner*—Linda C Dvorak
*Assistant Examiner*—Samantha Muro

(57) ABSTRACT

A gastric restrictor assembly for positioning within the digestive tract, e.g., stomach, of a patient to treat obesity is disclosed. The gastric restrictor assembly includes an attachment mechanism for attaching the assembly within a body lumen and a valve assembly for adjusting the diameter of a throughbore defined by valve assembly. The gastric restrictor includes first and second actuators which can be actuated transorally for operating the attachment mechanism and the valve assembly.

25 Claims, 6 Drawing Sheets

U.S. PATENT DOCUMENTS

| | | |
|---|---|---|
| 6,666,817 B2 | 12/2003 | Li |
| 6,675,809 B2 | 1/2004 | Stack et al. |
| 6,676,674 B1 | 1/2004 | Dudai |
| 6,726,696 B1 | 4/2004 | Houser et al. |
| 6,730,014 B2 | 5/2004 | Wilk |
| 6,740,121 B2 | 5/2004 | Geitz |
| 6,746,460 B2 | 6/2004 | Gannoe et al. |
| 6,752,754 B1 | 6/2004 | Feng et al. |
| 6,755,869 B2 | 6/2004 | Geitz |
| 6,758,219 B2 | 7/2004 | Sapala et al. |
| 6,773,440 B2 | 8/2004 | Gannoe et al. |
| 6,773,441 B1 | 8/2004 | Laufer et al. |
| 6,776,789 B2 | 8/2004 | Bryant et al. |
| 6,790,214 B2 | 9/2004 | Kraemer et al. |
| 6,802,868 B2 | 10/2004 | Silverman et al. |
| 6,808,483 B1 | 10/2004 | Ortiz et al. |
| 6,826,428 B1 | 11/2004 | Chen et al. |
| 7,175,660 B2 * | 2/2007 | Cartledge et al. .......... 623/2.11 |
| 2001/0011543 A1 | 8/2001 | Forsell |
| 2001/0034470 A1 | 10/2001 | Whalen et al. |
| 2002/0022851 A1 | 2/2002 | Kalloo et al. |
| 2002/0028979 A1 | 3/2002 | Silverman et al. |
| 2002/0052538 A1 | 5/2002 | Lau et al. |
| 2002/0065449 A1 | 5/2002 | Wardle |
| 2002/0091395 A1 | 7/2002 | Gabbay |
| 2002/0116013 A1 | 8/2002 | Gleason et al. |
| 2002/0151763 A1 | 10/2002 | Cook et al. |
| 2002/0169464 A1 | 11/2002 | Latour |
| 2002/0183768 A1 | 12/2002 | Deem et al. |
| 2002/0188354 A1 | 12/2002 | Peghini |
| 2002/0198548 A1 | 12/2002 | Robert |
| 2003/0032857 A1 * | 2/2003 | Forsell ........................ 600/30 |
| 2003/0040804 A1 | 2/2003 | Stack et al. |
| 2003/0040808 A1 | 2/2003 | Stack et al. |
| 2003/0088148 A1 | 5/2003 | Forsell |
| 2003/0092962 A1 | 5/2003 | Forsell |
| 2003/0109931 A1 | 6/2003 | Geitz |
| 2003/0120288 A1 | 6/2003 | Benchetrit |
| 2003/0130670 A1 | 7/2003 | Anderson et al. |
| 2003/0144575 A1 | 7/2003 | Forsell |
| 2003/0158564 A1 | 8/2003 | Benchetrit |
| 2003/0158569 A1 | 8/2003 | Wazne |
| 2003/0158601 A1 | 8/2003 | Silverman et al. |
| 2003/0171768 A1 | 9/2003 | McGhan |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208212 A1 | 11/2003 | Cigaina |
| 2003/0212306 A1 | 11/2003 | Banik |
| 2003/0225311 A1 | 12/2003 | Sayet et al. |
| 2004/0006351 A1 | 1/2004 | Gannoe et al. |
| 2004/0030347 A1 | 2/2004 | Gannoe et al. |
| 2004/0039452 A1 | 2/2004 | Bessler |
| 2004/0044357 A1 | 3/2004 | Gannoe et al. |
| 2004/0045562 A1 | 3/2004 | Sapala et al. |
| 2004/0049209 A1 | 3/2004 | Benchetrit |
| 2004/0059289 A1 | 3/2004 | Garza Alvarez |
| 2004/0082963 A1 | 4/2004 | Gannoe et al. |
| 2004/0089313 A1 | 5/2004 | Utley et al. |
| 2004/0093091 A1 | 5/2004 | Gannoe et al. |
| 2004/0097989 A1 | 5/2004 | Molina Trigueros |
| 2004/0107004 A1 | 6/2004 | Levine et al. |
| 2004/0116773 A1 | 6/2004 | Furness et al. |
| 2004/0117031 A1 | 6/2004 | Stack et al. |
| 2004/0122455 A1 | 6/2004 | Lin |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133219 A1 | 7/2004 | Forsell |
| 2004/0138684 A1 | 7/2004 | Eton |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0147810 A1 | 7/2004 | Mizuno |
| 2004/0148034 A1 * | 7/2004 | Kagan et al. ............. 623/23.65 |
| 2004/0158272 A1 | 8/2004 | Hofle et al. |
| 2004/0158331 A1 * | 8/2004 | Stack et al. ............. 623/23.65 |
| 2004/0167561 A1 | 8/2004 | Boucher et al. |
| 2004/0172141 A1 | 9/2004 | Stack et al. |
| 2004/0172142 A1 | 9/2004 | Stack et al. |
| 2004/0193261 A1 * | 9/2004 | Berreklouw ............... 623/2.11 |
| 2004/0199196 A1 | 10/2004 | Ravo |
| 2004/0204722 A1 | 10/2004 | Sikora et al. |
| 2004/0204768 A1 | 10/2004 | Geitz |
| 2004/0209538 A1 | 10/2004 | Klinge et al. |
| 2004/0210243 A1 | 10/2004 | Gannoe et al. |
| 2004/0220682 A1 * | 11/2004 | Levine et al. ............ 623/23.65 |
| 2004/0230137 A1 | 11/2004 | Mouton |
| 2004/0243152 A1 | 12/2004 | Taylor et al. |
| 2004/0254537 A1 | 12/2004 | Conlon et al. |
| 2004/0260316 A1 | 12/2004 | Knudson et al. |
| 2004/0267293 A1 | 12/2004 | Byrum et al. |
| 2005/0004430 A1 | 1/2005 | Lee et al. |
| 2005/0004681 A1 | 1/2005 | Stack et al. |
| 2005/0038458 A1 | 2/2005 | Bailly et al. |
| 2005/0049718 A1 | 3/2005 | Dann et al. |
| 2005/0055039 A1 | 3/2005 | Burnett et al. |
| 2005/0070931 A1 | 3/2005 | Li et al. |
| 2005/0075652 A1 | 4/2005 | Byrum et al. |
| 2005/0080317 A1 | 4/2005 | Merade |
| 2005/0085688 A1 | 4/2005 | Girard et al. |
| 2005/0085835 A1 | 4/2005 | Rennich |
| 2005/0085923 A1 | 4/2005 | Levine et al. |
| 2005/0090844 A1 | 4/2005 | Patel et al. |

* cited by examiner

GASTRIC RESTRICTOR ASSEMBLY AND METHOD OF USE

BACKGROUND

1. Technical Field

The present disclosure relates to a surgical implant for treating obesity in a patient. More particularly, the present disclosure relates to a surgical implant for constricting the stomach of a patient to treat obesity in a patient.

2. Background of Related Art

A variety of different approaches are known for the treatment of obesity in a patient. These approaches can be of the non-surgical variety, e.g., dieting, or of the surgical variety, e.g., gastric bypass, small bowel bypass etc. Where non-invasive non-surgical procedures such as dieting rely on the will power of a patient and may not be effective, invasive surgical procedures such as bypass surgery can be risky and have undesirable side effects. As such, less invasive surgical devices for constricting or reducing the capacity of the digestive tract, e.g., the stomach have been developed. These devices include gastric bands which are positioned about the stomach to constrict the stomach and devices such as inflatable balloons for reducing the reservoir capacity of the stomach. Each of these types of devices produce a sense of satiety in a patient to reduce the patient's desire to ingest food.

Although the above-identified devices have had some success, improvements to these devices would be desirable.

SUMMARY

In accordance with the present disclosure, a gastric restrictor assembly is provided which includes a housing, a valve assembly and an attachment mechanism. In one embodiment, the valve assembly is supported within the housing and includes a first member, a second member and a plurality of vanes which define a throughbore. The plurality of vanes are pivotally supported about a pivot member on the first member and the first member is fixedly secured within the housing. The second member is rotatably secured to the first member and includes a plurality of cam members. Each of the cam members is positioned within a slot formed in one of the plurality of vanes. The second member is movable in relation to the first member to move the cam members within the slots to effect pivoting of the vanes about the pivot members. The second member is movable between a first position and a second position to move the vanes between a first position defining a minimum throughbore diameter and a second position defining a maximum throughbore diameter.

In one embodiment, the first member includes a first ring or annular member and the second member includes a second ring or annular member. The second ring member includes gear teeth positioned at least partially about its periphery. An actuator is rotatably supported on the housing and includes gear teeth positioned to mesh with the gear teeth of the second ring member to move the second ring member between its first and second positions.

In one embodiment, the attachment mechanism includes a plurality of arcuate fastening members or hoops and a drive ring. Each hoop can include a pointed or sharpened tip and an arcuate body having a plurality of threads formed thereon. The drive ring includes an inner surface having a plurality of gear teeth and an outer surface having a helical thread. The fastening members are positioned at least partially within the housing such that each fastening member extends through or is positioned to extend through an opening in the housing. The helical thread of the drive ring is positioned to engage the plurality of the threads on the arcuate body of each fastening member such that upon movement of the drive ring in relation to the fastening member, each fastening member is moved between a retracted position and a deployed or advanced position.

In one embodiment, the inner surface of the drive ring includes gear teeth which are positioned to mesh with the gear teeth of a drive ring actuator. The drive ring actuator is actuable to effect rotation of the drive ring in relation to the plurality of fastening members.

In one embodiment, an attachment mechanism actuation tool is provided to actuate the drive ring actuator and a valve assembly adjustment tool is provided to actuate the second member of the valve assembly. Both the attachment mechanism actuation tool and the valve assembly adjustment tool can be configured and dimensioned for transoral actuation of the attachment mechanism and the valve assembly, respectively.

BRIEF DESCRIPTION OF THE DRAWINGS

Various embodiments of the presently disclosed gastric restrictor assembly are disclosed herein with reference to the drawings, wherein.

DETAILED DESCRIPTION OF EMBODIMENTS

Figure 1:
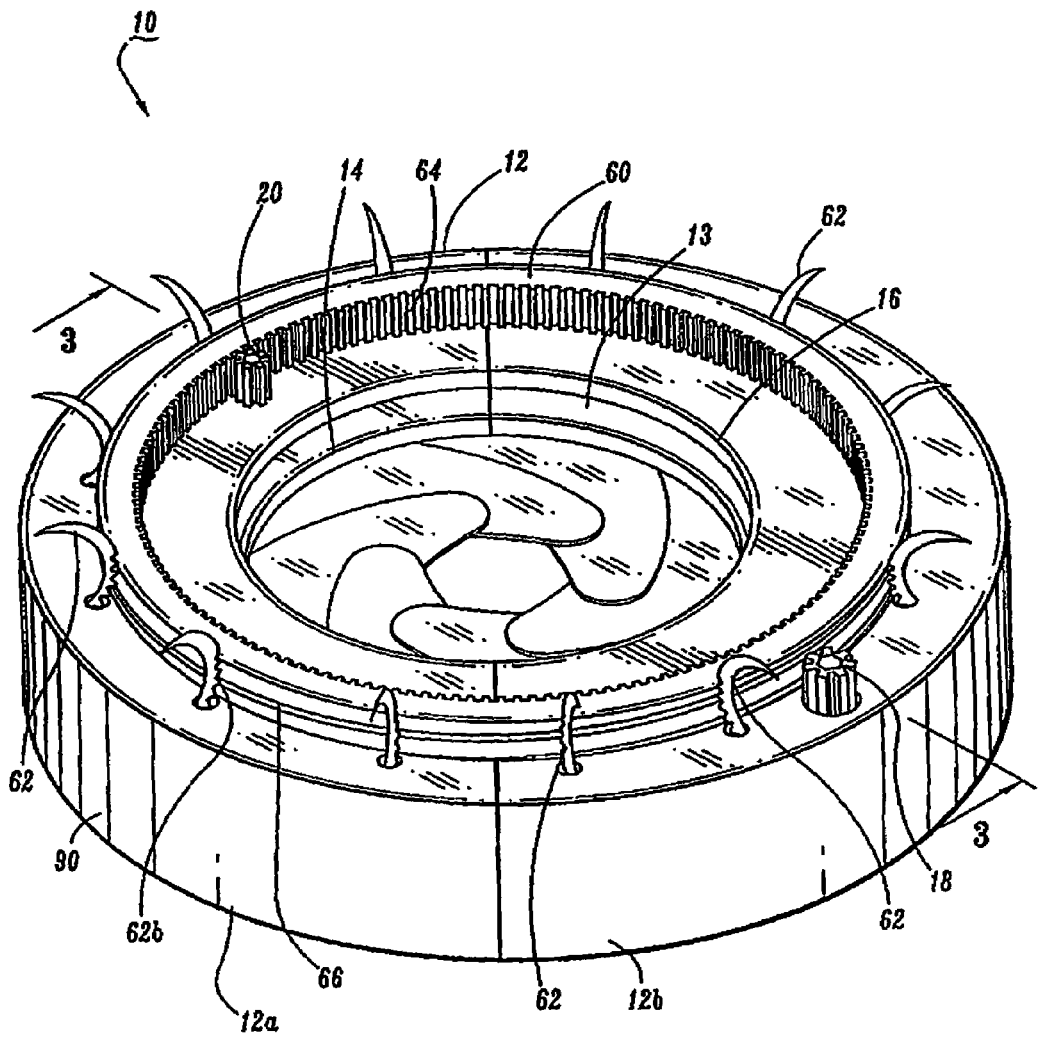
FIG. 1 is a top perspective view of one embodiment of the presently disclosed gastric restrictor assembly.

Embodiments of the presently disclosed gastric restrictor assembly and its method of use will now be described in detail with reference to the drawings in which like reference numerals designate identical or corresponding elements in each of the several views.

FIG. 1 illustrates one embodiment of the presently disclosed gastric restrictor assembly shown generally as 10. Gastric restrictor assembly 10 includes an annular housing 12 which defines a thoughbore 13 and supports a valve assembly 14 and an attachment mechanism 16. In one embodiment, housing 12 is formed from half-sections 12a and 12b which are fastened together to enclose valve assembly 14 and attachment mechanism 16. Actuators 18 and 20 are positioned on a top surface of housing 12 to facilitate operation of valve assembly 14 and attachment mechanism 16, respectively, as will be described in further detail below.

Figure 2:
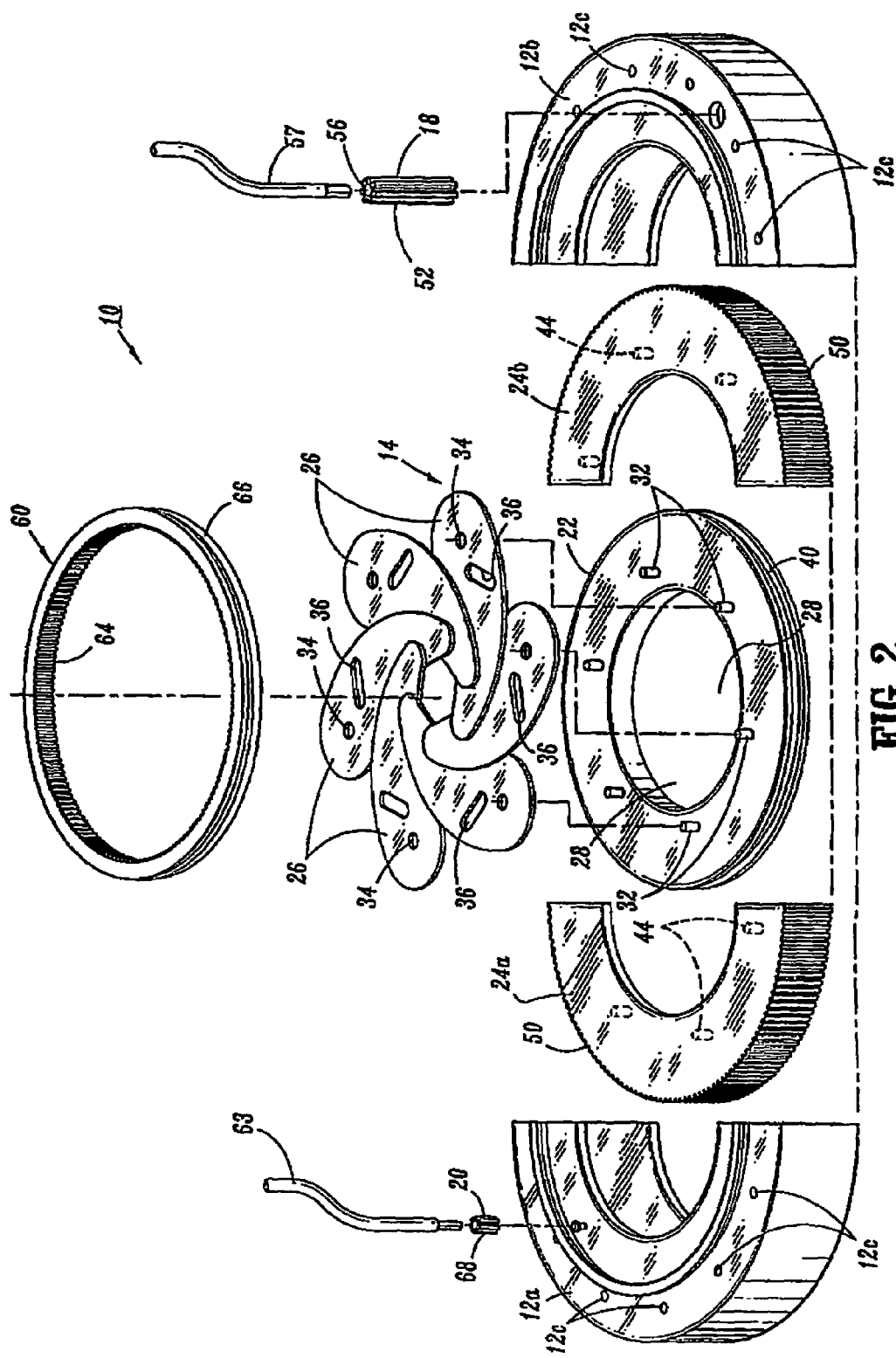
FIG. 2 is a top perspective, exploded view of the valve assembly and attachment mechanism of the gastric restrictor assembly shown in FIG. 1.
Figure 3:
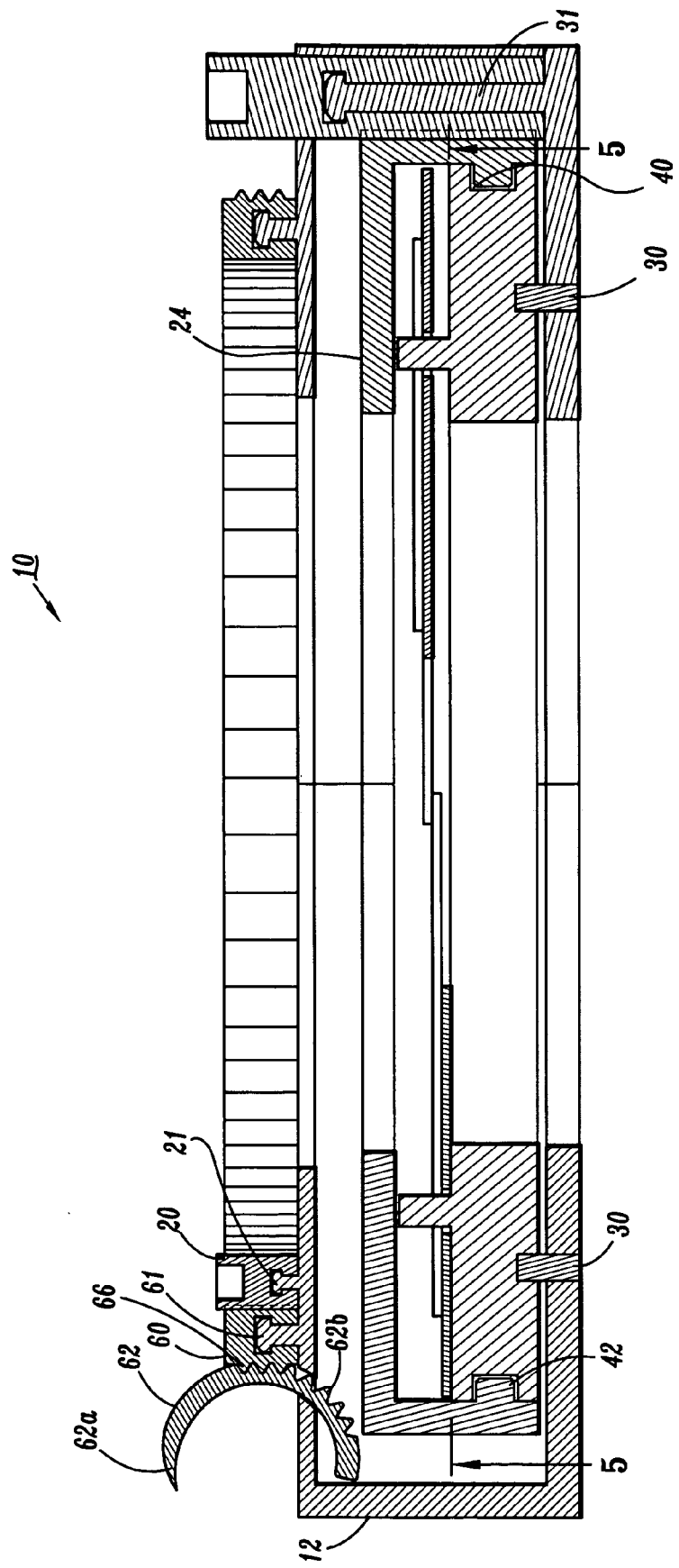
FIG. 3 is a cross-sectional view taken along section lines 3-3 of FIG. 1.
Figure 4:
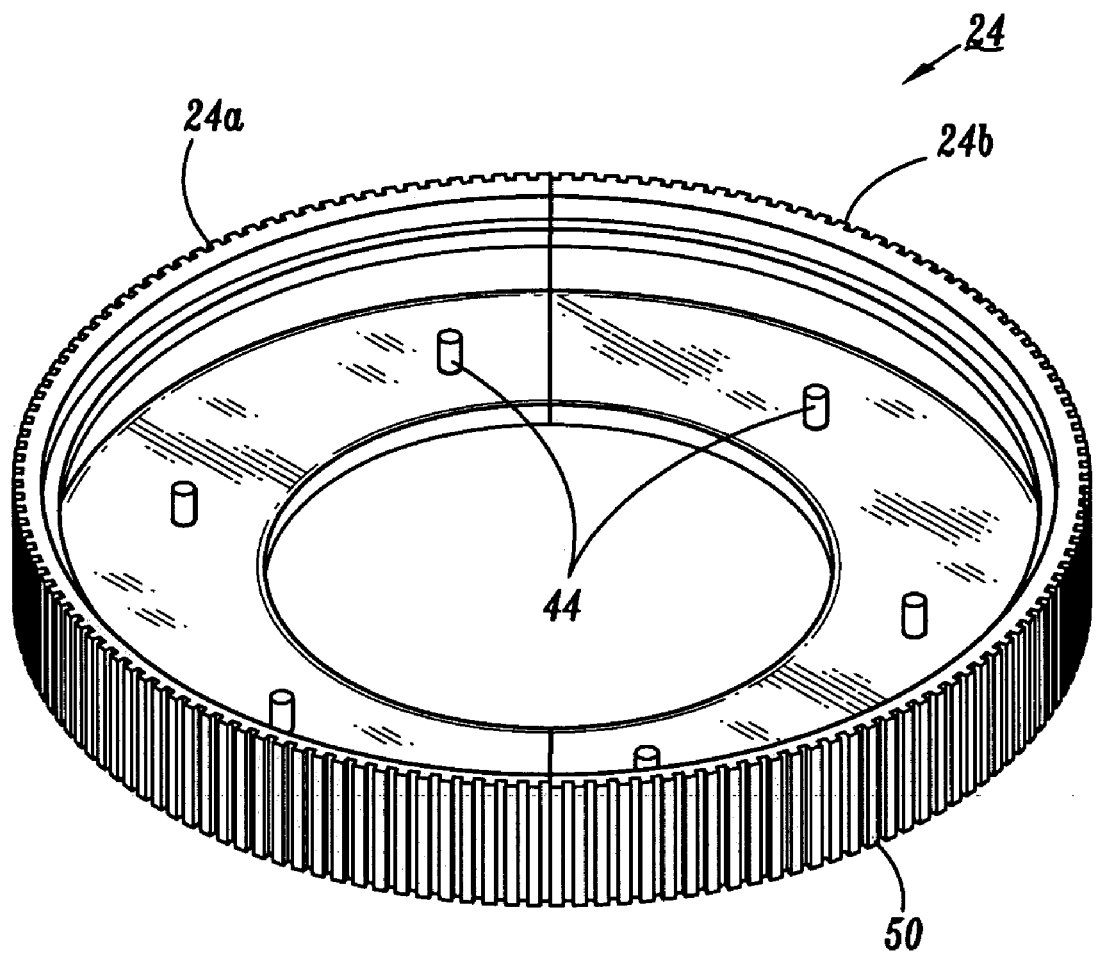
FIG. 4 is a bottom perspective view of the second member of the valve assembly of the gastric restrictor assembly shown in FIG. 3.
Figure 5:
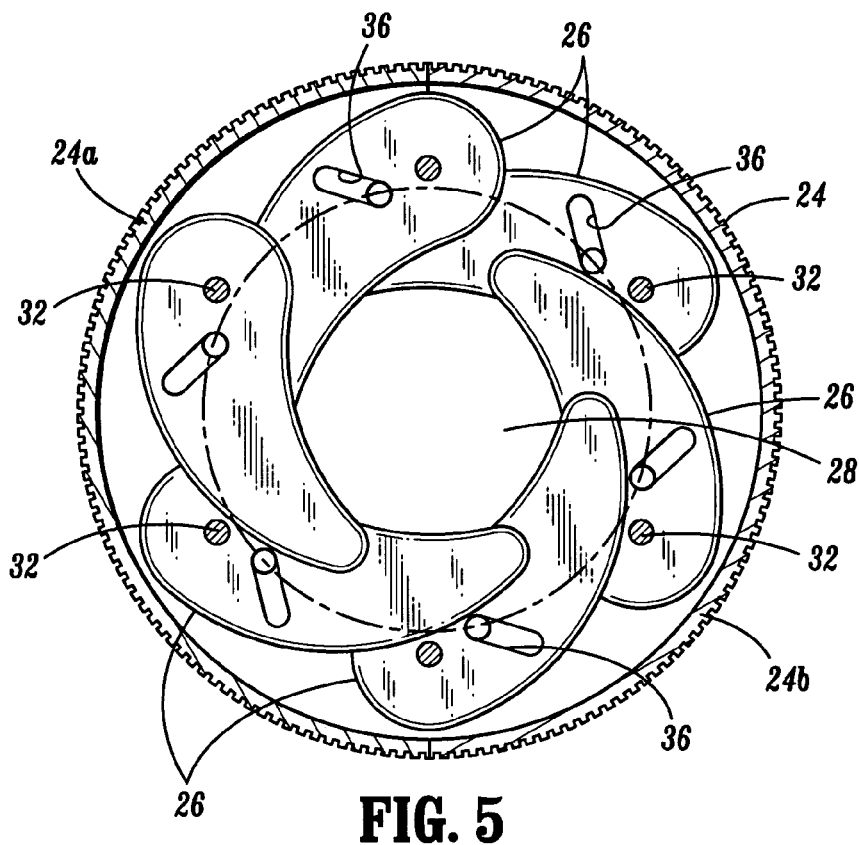
FIG. 5 is a top cross-section view of the gastric restrictor assembly shown in FIG. 1 illustrating the throughbore of the assembly in its maximum diameter position.
Figure 6:
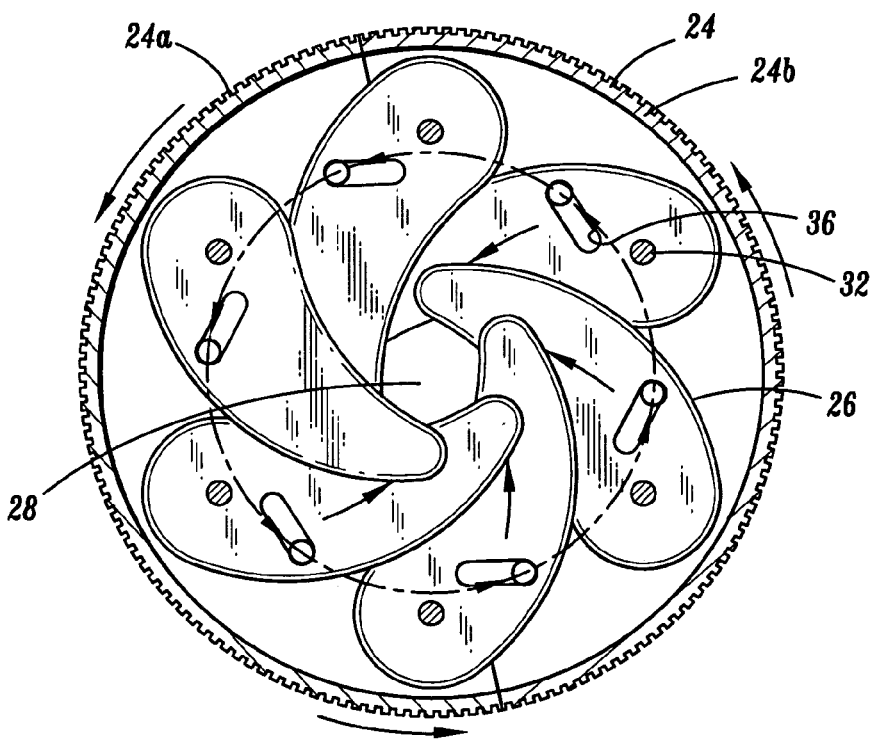
FIG. 6 is a top cross-sectional view of the gastric restrictor assembly shown in FIG. 1 illustrating the throughbore of the valve assembly in its minimum diameter position.
Figure 7:
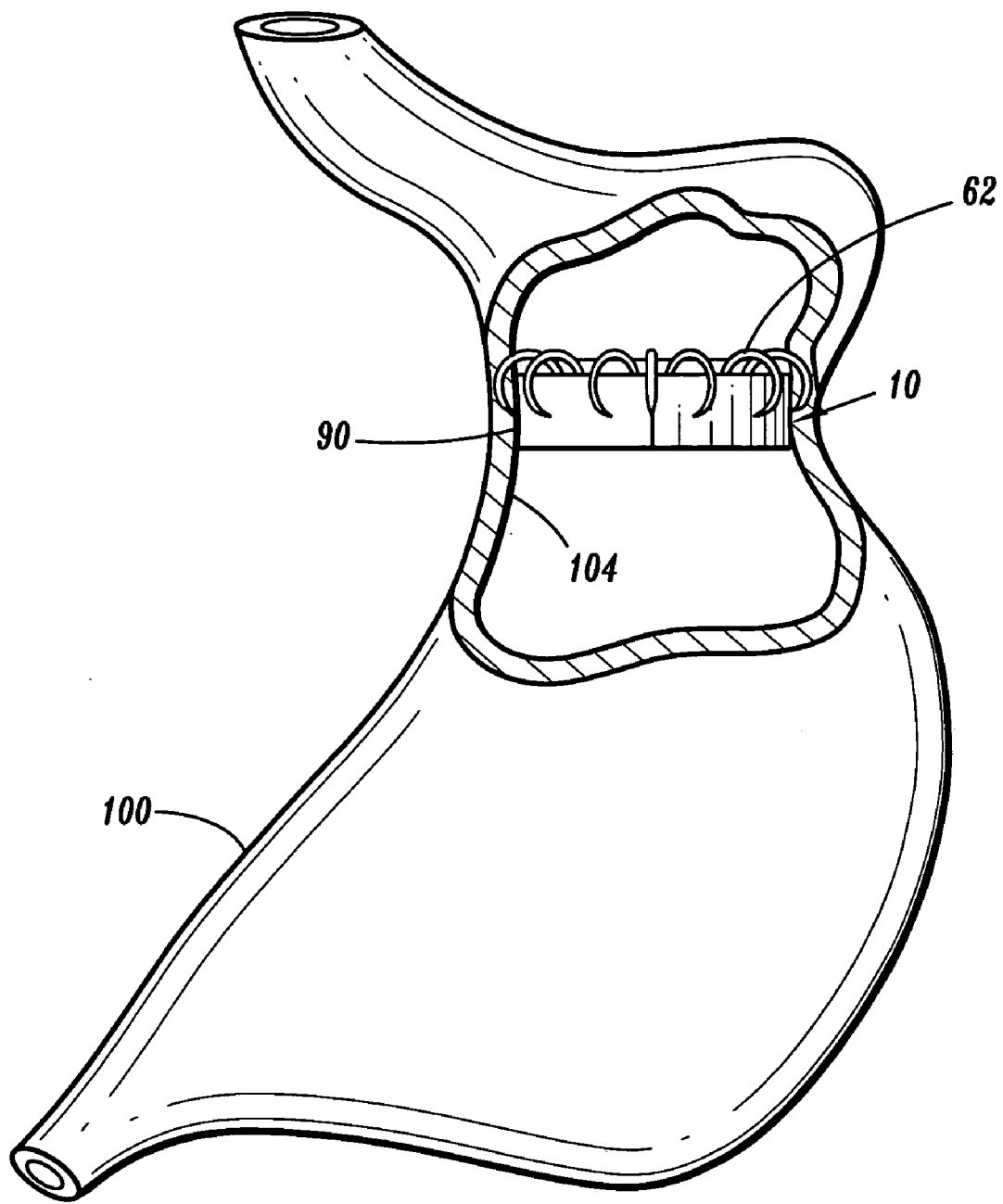
FIG. 7 is a side view of the gastric restrictor assembly shown in FIG. 1 attached to an internal wall of the stomach with a portion of the stomach cutaway.

Referring to FIGS. 2-4, valve assembly 14 includes actuator 18, a first member 22, a second member 24 (FIG. 3) and a multiplicity of vanes 26. First and second members 22 and 24 may be in the form of first and second rings which define a throughbore 28 which is substantially coaxial with throughbore 13 of housing 12. First member 22 is rotatably fixed to a bottom inner wall of housing 12 such as by pins 30. A plurality of pivot members 32 are spaced about first member 22. Each pivot member 32 is positioned and dimensioned to be received in a hole 34 formed in a respective vane 26 such that vanes 26 are pivotally supported on first member 22. Each vane 26 includes an elongated slot 36. It is envisioned that pivot members 32 may be formed integrally with housing 12 and first member 22 can be eliminated from assembly 10.

Second member 24 is rotatably mounted to first member 22. In one embodiment, second member 24 includes first and second half-sections 24a and 24b which are fastened about first member 22. First member 22 includes an annular recess 40 which is dimensioned to receive an annular rib 42 formed about an inner wall of second member 24 (FIG. 3). Positioning of rib 42 within annular recess 40 of first member 22 rotatably fastens second member 24 to first member 22.

Second member 24 includes a plurality of cam members 44 which are positioned on an inner wall of second member 24. Cam members 44 are received in respective slots 36 of vanes 26. Slots 36 of vanes 26 are configured such that rotation of second member 24 in relation to first member 22 effects movement of vanes 26 either into or out from throughbore 28. Vanes 26 define an iris valve for selectively adjusting the diameter or cross-sectional area of throughbore 28. Although throughbore 28 is illustrated as being circular, other non-circular configurations are envisioned, e.g., rectangular, square, oblong, etc.

In one embodiment, the outer periphery of second member 24 includes a series of gear teeth 50. Actuator 18 also includes a series of gear teeth 52. Gear teeth 52 are positioned to mesh with gear teeth 50 such that rotation of actuator 18 effects rotation of second member 24 in relation to first member 22. Alternately, gear teeth 50 may only extend over a portion of the outer periphery of second member 24. As discussed above, rotation of second member 24 in relation to first member 22 effects movement of vanes 26 to selectively vary the diameter or cross-sectional area of thoughbore 28. It is envisioned that other types of actuators may be employed to operate valve assembly 14.

Actuator 18 is rotatably mounted about a post 31 (FIG. 3) formed on housing 12 and includes engagement structure 56 for engaging a valve assembly adjustment tool 57. Engagement structure 56 may include a hexagonal recess. Alternately, other engagement structure including internal and external interlocking configurations may be used.

Referring again to FIGS. 2 and 3, attachment mechanism 16 includes a drive member or ring 60 and a plurality of fastening elements or hoops 62 (FIG. 3) which are spaced about ring 60. Ring 60 is rotatably mounted on a circular rail 61 formed on housing 12. Alternately, ring 60 can be rotatably secured to housing 12 using other known fastening techniques. It is envisioned that fastening elements 62 may comprise configurations other than hoops or, alternately, include a single element having one or more attachment surfaces. In one embodiment, ring 60 includes an inner gear surface 64 and an outer surface defining a helical thread 66. Each hoop 62 includes a tip 62a which may be pointed and a series of teeth or worm gear segments 62b positioned to engage helical thread 66 of ring 60.

Actuator 20 is rotatably mounted about a post 21 formed on an outer surface of housing 12 and includes gear teeth 68 which are positioned to mesh with gear surface 64 of drive ring 60. When actuator 20 is rotated within housing 12, drive ring 60 is also driven in rotation by engagement of gear teeth 68 with gear surface 64. As drive ring 60 rotates, helical threads 66 engage teeth 62b (FIG. 3) of each of hoops 62 to advance tips 62a of hoops 62 through openings 12c of housing 12 along a substantially arcuate path. As will be discussed in further detail below, hoops 62 function to secure gastric restrictor assembly 10 within a body lumen. An attachment mechanism actuation tool 63, which can be configured for transoral use, is provided to operate actuator 20.

Referring to FIGS. 1 and 5-7, during installation of gastric restrictor assembly 10 into a body lumen, e.g., the stomach 100, gastric restrictor assembly 10 is positioned within stomach transorally. Alternately, gastric restrictor assembly 10 can be positioned with a body lumen during an open surgical procedure. The outer wall 90 of housing 12 is positioned adjacent an inner wall of stomach 100. Next, actuator 20 (FIG. 1) is operated to rotate drive ring 60. As drive ring 60 is rotated within housing 12, helical threads 66, which engage teeth 62b of hoops 62, advances each of hoops 62 from within housing 12 along an arc-shaped path through a portion of inner wall 104 of stomach 100. The arc-shaped path or curvature of hoops 62 should be such as to advance tips 62a of hoops 62 through only a portion of inner wall 104 of stomach 100 without fully penetrating wall 104 of stomach 100. This will prevent gastric fluids from exiting the stomach into the abdominal cavity. It is envisioned that the shape of hoops 62 may be changed to alter the path of travel of hoops 2 to effect full penetration of a wall of a body lumen if desired. Engagement of hoops 62 with wall 104 of stomach 100 secures gastric restrictor assembly 10 to inner wall 104 of stomach 100. Although a multiplicity of hoops are illustrated in FIG. 1, two or more hoops need only be provided to secure assembly 10 within the stomach.

When gastric restrictor assembly 10 is secured within the stomach, throughbore 28 of valve assembly 14 defines a passage through the stomach. The diameter of throughbore 28 can be selectively intraorally adjusted from a maximum diameter shown in FIG. 5 to a minimum diameter shown in FIG. 6 using valve assembly adjustment tool 57. As discussed above, adjustment tool 57 (FIG. 2) operates actuation member 18 to reposition vanes 26 of valve assembly 14.

It will be understood that various modifications may be made to the embodiments disclosed herein. For example, the actuation mechanism for the valve assembly and/or the attachment mechanism not be gear driven but rather may include other types of drive mechanism, e.g., cam mechanism, etc. Further, the gastric restrictor assembly may be positioned at any position in the digestive tract where restriction may be warranted or desired. Therefore, the above description should not be construed as limiting, but merely as exemplifications of embodiments. Those skilled in the art will envision other modifications within the scope and spirit of the claims appended hereto.

What is claimed is:

1. A gastric restrictor assembly comprising:
a housing;
a valve assembly supported within the housing, the valve assembly defining a throughbore through the housing and being actuable to selectively adjust an area of the throughbore;
an attachment mechanism supported by the housing, the attachment mechanism having at least one fastening element and being actuable to move the at least one fastening element to a position securing the gastric restrictor assembly to an inner wall of a lumen;
a first actuator supported on the housing and operatively associated with valve assembly, the first actuator being positioned to be transorally actuable to operate the valve assembly and to selectively adjust the area of the throughbore; and a second actuator supported on the housing and operatively associated with the attachment mechanism, the second actuator being positioned to be transorally actuable to move the at least one fastening element to a position securing the gastric restrictor assembly to an inner wall of a lumen, wherein the at least one fastening element includes a plurality of arcuate hoops positioned about the housing, the hoops being movable from a first position located substantially within the housing to a second position extending from the housing, wherein each of the hoops includes an arcuate body having a series of teeth formed thereon, and wherein the attachment mechanism further includes a drive member, the drive member including a helical thread which is positioned to mesh with the teeth of each of the hoops, the drive member being movable to move the helical thread in relation to the hoop teeth to advance each of the hoops from the first position to the second position.

2. A gastric restrictor assembly according to claim 1, wherein each of the arcuate hoops has a tip configured to penetrate body tissue.

3. A gastric restrictor assembly according to claim 1, wherein the drive member includes a drive ring which is rotatably supported on the housing.

4. A gastric restrictor assembly according to claim 3, wherein the drive ring includes an inner gear surface and an outer surface defining the helical thread.

5. A gastric restrictor assembly according to claim 4, further including a first actuator rotatably supported by the housing, the first actuator including gear teeth positioned to mesh with inner gear surface of the drive ring.

6. A gastric restrictor assembly according to claim 1, wherein the valve assembly includes a plurality of vanes which can be selectively repositioned transorally by the first actuator to change the area of the valve assembly throughbore.

7. A gastric restrictor assembly according to claim 6, wherein the valve assembly further includes a first stationary member and a second movable member, the plurality of vanes being pivotally secured to the first stationary member, and the second movable member being movable between a first position and a second position to change the area of the throughbore.

8. A gastric restrictor assembly according to claim 7, wherein the second movable member includes a plurality of cam members and each of the plurality of vanes includes a slot dimensioned to receive one of the plurality of cam members.

9. A gastric restrictor assembly according to claim 8, wherein the second movable member includes a rotatable ring, the rotatable ring having a plurality of gear teeth positioned to engage an actuator rotatably supported on the housing.

10. A method for restricting a portion of the digestive tract comprising the following steps:
i) positioning a gastric restrictor assembly within a portion of the digestive tract, the gastric restrictor assembly including a valve assembly defining a throughbore and an attachment mechanism including at least one fastening element for securing the gastric restrictor assembly within the digestive tract; and
ii) actuating the attachment mechanism to secure the gastric assembly within the digestive tract,
wherein the at least one fastening element includes a plurality of arcuate hoops positioned about the housing, the hoops being movable from a first position located substantially within the housing to a second position extending from the housing,
wherein each of the hoops includes an arcuate body having a series of teeth formed thereon, and
wherein the attachment mechanism further includes a drive member, the drive member including a helical thread which is positioned to mesh with the teeth of each of the hoops, the drive member being movable to move the helical thread in relation to the hoop teeth to advance each of the hoops from the first position to the second position.

11. A method according to claim 10, wherein the positioning step and the actuating step are performed transorally.

12. A method according to claim 10, wherein the portion of the digestive tract is the stomach.

13. A method according to claim 10, further including the step of operating the valve assembly to change the cross-sectional area of the throughbore.

14. A method according to claim 13, wherein the operating step is performed transorally.

15. A method according to claim 11, further including the step of operating the valve assembly to change the cross-sectional area of the throughbore.

16. A method according to claim 15, wherein the operating step is performed transorally.

17. A gastric restrictor assembly comprising:
a housing;
a valve assembly supported within the housing, the valve assembly defining a throughbore through the housing and being actuable to selectively adjust an area of the throughbore; and
an attachment mechanism supported by the housing, the attachment mechanism having at least one fastening element and being actuable to move the fastening element to a position securing the gastric restrictor assembly to an inner wall of a lumen,
wherein the at least one fastening element includes a plurality of arcuate hoops positioned about the housing, the hoops being movable from a first position located substantially within the housing to a second position extending from the housing,
wherein each of the hoops includes an arcuate body having a series of teeth formed thereon, and
wherein the attachment mechanism further includes a drive member, the drive member including a helical thread which is positioned to mesh with the teeth of each of the hoops, the drive member being movable to move the helical thread in relation to the hoop teeth to advance each of the hoops from the first position to the second position.

18. A gastric restrictor assembly according to claim 17, wherein each of the hoops includes an arcuate body having a tip configured to penetrate body tissue.

19. A gastric restrictor assembly according to claim 17, wherein the drive member includes a drive ring which is rotatably supported on the housing.

20. A gastric restrictor assembly according to claim 19, wherein the drive ring includes an inner gear surface and an outer surface defining the helical thread.

21. A gastric restrictor assembly according to claim 20, further including a first actuator rotatably supported by the housing, the first actuator including gear teeth positioned to mesh with inner gear surface of the drive ring.

22. A gastric restrictor assembly according to claim 17, wherein the valve assembly includes a plurality of vanes which can be selectively repositioned to change the area of the valve assembly throughbore.

23. A gastric restrictor assembly according to claim 22, wherein the valve assembly further includes a first stationary member and a second movable member, the plurality of vanes being pivotally secured to the first stationary member, and the second movable member being movable between a first position and a second position to change the area of the throughbore.

24. A gastric restrictor assembly according to claim 23, wherein the second movable member includes a plurality of cam members and each of the plurality of vanes includes a slot dimensioned to receive one of the plurality of cam members.

25. A gastric restrictor assembly according to claim 24, wherein the second movable member includes a rotatable ring, the rotatable ring having a plurality of gear teeth positioned to engage an actuator rotatably supported on the housing.

* * * * *